United States Patent [19]
Choukroun

[11] Patent Number: 6,013,073
[45] Date of Patent: Jan. 11, 2000

[54] INSTRUMENT INTENDED TO THE LOCATION OF VEINS BY MEANS OF OPTICAL FIBERS AND TO THE SIMULTANEOUS ABLATION THEREOF

[75] Inventor: Pierre-Louis Choukroun, Paris, France

[73] Assignee: MXM, Antibes, France

[21] Appl. No.: 08/945,471

[22] PCT Filed: May 22, 1996

[86] PCT No.: PCT/FR96/00760

§ 371 Date: Nov. 20, 1997

§ 102(e) Date: Nov. 20, 1997

[87] PCT Pub. No.: WO96/37143

PCT Pub. Date: Nov. 28, 1996

[30] Foreign Application Priority Data

May 22, 1995 [FR] France .................................. 95 06051

[51] Int. Cl.[7] .................................................. A61B 17/36
[52] U.S. Cl. ............................ 606/15; 607/88; 606/159
[58] Field of Search ..................................... 606/1, 15–16, 606/159; 607/88

[56] References Cited

U.S. PATENT DOCUMENTS

| | | |
|---|---|---|
| 3,641,332 | 2/1972 | Reick et al. . |
| 5,022,399 | 6/1991 | Biegleisen . |
| 5,047,013 | 9/1991 | Rossdeutscher . |
| 5,152,277 | 10/1992 | Honda et al. . |
| 5,209,748 | 5/1993 | Daikuzono ................................. 606/16 |
| 5,282,798 | 2/1994 | Bruse et al. ............................... 606/17 |
| 5,536,265 | 7/1996 | Van Der Bergh et al. ................. 606/2 |
| 5,737,472 | 4/1998 | Bernasson et al. ...................... 385/123 |

FOREIGN PATENT DOCUMENTS

| | | |
|---|---|---|
| 2133338 | 11/1972 | France . |
| 93/15401 | 5/1995 | France . |
| 3603782 | 10/1987 | Germany . |
| 1357156 | 6/1974 | United Kingdom . |
| 2198955 | 6/1988 | United Kingdom ............. A61N 5/06 |
| WO 93/06769 | 4/1993 | WIPO . |

*Primary Examiner*—Linda C. M. Dvorak
*Assistant Examiner*—Roy Gibson
*Attorney, Agent, or Firm*—Wolf, Greenfield & Sacks, P.C.

[57] ABSTRACT

The technical field is that of instruments for medical examination of ducts in the body by visual examination using an illuminating device, and also making it possible, where appropriate, to act surgically in said ducts. The invention provides an instrument intended mainly for locating veins and simultaneously removing them, the elongate central body of the instrument having at least one optical fiber connected at one end to a light source; according to the invention, said instrument is such that said optical fiber is a fiber that diffuses light laterally and radially relative to its axis XX', and it is provided at its distal end that is not connected to the light source with a transparent head having an outside diameter greater than that of said central body.

23 Claims, 1 Drawing Sheet

INSTRUMENT INTENDED TO THE LOCATION OF VEINS BY MEANS OF OPTICAL FIBERS AND TO THE SIMULTANEOUS ABLATION THEREOF

The present invention relates to an instrument intended mainly for locating veins by optical fiber, and for simultaneously ablating them.

FIELD OF THE INVENTION

The technical field of the invention is that of instruments for medically examining ducts in the body by visual examination with a lighting device, and also capable, where appropriate, of acting surgically in said ducts.

BACKGROUND OF THE INVENTION

The main application of the invention is locating the paths followed by veins, for the purpose of extracting varices by various vein-removal techniques, which at present comprise:

either exo-removal of veins performed in various different ways:

by a stripper provided with a ball which "tears out" the vein, disconnecting it from the tissue surrounding the vein: this technique is described in French patent application No. FR 2 133 338 published on Oct. 30, 1972, using "an instrument made of synthetic plastics material, for surgically 'rodding' veins";

by devices for exo-removal of veins by means of rings acting in a manner similar to that of a stripper; or by phlebectomy using a hook which draws the vein through a mini-incision and, by pulling and dissection, brings it to the outside, enabling it to be removed by a varying number of incisions;

or by endo-removal of veins or invaginaton in which the vein is turned insideout like "a glove finger", with the vein being withdrawn by traction applied inside the lumen of the vessel, which method is less traumatizing for nerve structures in the vicinity of the veins. The same principle is applied when removing veins on rods.

Nevertheless, all of those methods encounter a problem of identifying the paths followed by the veins and require dissection, which becomes more difficult with increasing fat, edema, skin state, and the presence of trophic complaints or panniculitis.

At present, to perform such localization, preoperative clinical examination and Doppler echography are used to better locate the paths of veins and to draw them directly on the skin, however these lines drawn on a standing subject are offset during the operation where the patient is reclining, dorsally or ventrally.

Locating techniques are also known in which a point of the body is lighted internally by using optical fibers which are inserted from outside the body into the chosen duct, such as a vein: an external light source is then connected to the end of the fibers situated outside the body, and the fibers guide the light to the other or "distal" end, i.e. the end which has penetrated into said duct and is furthest from said light source, at which point they illuminate the vein around their ends, like a spotlight. One such technique is described in German patent application No. DE 3 603 782 published on Oct. 15, 1987 which teaches a probe comprising firstly a central channel through which liquids can be inserted, and secondly optical fibers distributed around the periphery of the channel and situated in the wall thickness of the probe to provide illumination at the end thereof in the event of a blockage occurring as a surgical instrument for operating in a vein is progressing: it is then possible to locate the position of the blockage from outside the body by transillumination, i.e. by the transmission of light through tissue, and then decide what action to take; that therefore constitutes an instrument for locating a point only, and it cannot be used for extracting varices, neither by exo-removal of veins nor by endo-removal of veins, which require a different instrument such as described above and which specifically could be the instrument which has blocked the vein.

OBJECT AND BRIEF SUMMARY OF THE INVENTION

The problem that arises is thus essentially that of being able firstly to locate the entire path of a vein so as to give a third dimension to the operator who can then mark out the light path on the surface and in depth, and simultaneously with the same instrument to remove veins either completely, or selectively and esthetically, specifically because of the path shown up by the light, thereby guiding exact incision and dissection of the vein.

A solution to the problem posed is an instrument intended for locating veins, and made up of an elongate central body constituted by at least one optical fiber connected at one end to a light source, said optical fiber being a fiber that diffuses light laterally and radially relative to its axis XX'; said central body is provided at its distal end which is not connected to the light source with a transparent head having an outside diameter greater than that of the central body; in a preferred embodiment, said central body has only a single one-piece optical fiber made of polymer, and preferably of polymethylmethacrylate. Said transparent end head may be a cylinder that tapers in a bullet shape; in addition, the last few centimeters of the central body behind said transparent head, e.g. the last 5 centimeters, may be helical or twisted in shape so as to have a vein-dilating effect, thereby facilitating advance of the instrument in a vein.

In a particular embodiment, said instrument may include a hollow operating channel disposed along said central body for injecting liquids close to the transparent head at the distal end, where the orifice is protected by the shoulder behind the head.

The shoulder also makes it possible to secure a thread by a simple loop capable of sliding over the central body of the instrument and coming into abutment against said shoulder, which thread serves to extract the vein by invagination and, in a particular embodiment, said instrument also includes a bullet-shaped cap covering said transparent head at the distal end, and can therefore enable conventional exo-removal of veins or rodding to be performed.

The result is a novel instrument intended both for simultaneously locating the entire path of a vein by transillumination thereof, and for ablation of varices by various techniques, and this has not been possible with any instrument in the past.

The optical fiber(s) diffusing light laterally and radially relative to the axis make it possible to illuminate the entire path of said vein, the transparent head at the distal end makes it possible to go past the valvulae of the veins and to fix a thread therein for removing veins by invagination, i.e. by turning the vein insideout like a glove, which can then be performed during the same operation as illuminating the vein; and because of the hollow operating channel disposed along the central body, it is possible optionally to inject contrast liquid or sclerosis-inducing liquid depending on the type of operation desired.

By way of example, such optical fibers for lateral illumination are described in French patent application 93/15401, now patent No. FR 2 714 147 published on Jun. 23, 1995, which teaches a cylindrical optical fiber structure allowing light to emerge laterally by means of a certain zone of its outside surface that includes a large number of close-together blemishes of very small size compared with the diameter of the fiber, each of the blemishes causing light that is being conveyed to emerge at that spot; the overall appearance of the fiber is thus luminous and the surface density of the blemishes varies along the propagation direction of the light flux so as to obtain substantially constant light density along the entire length of the fiber; other methods of manufacturing such fibers can include that described in PCT patent application No. 93/06769 published on Apr. 15, 1993 which describes a "bougie" system, which although not constituted by an optical fiber, nevertheless enables light to be diffused laterally by means of microscopic metal particles dispersed in said plastic, and serving to reflect light that can penetrate into said plastic towards the outside of its walls.

The set of characteristics combined in the present invention, even though some are known separately in other devices and applications, thus provide assistance and make certain kinds of surgery possible that no instrument has done in the past, thus making phlebectomy easier, "brighter" and more "illuminated".

As mentioned above, instruments for illuminating veins are indeed known since engioscopes serve to display valvulae and the ostia of veins, but simultaneous transillumination over the entire length of a vein path to facilitate simultaneous extraction is described for the first time in the present invention.

Another advantage of the invention is to prevent the instrument or stripper going "the wrong way": this happens fairly frequently with conventional instruments and can give rise either to the vein wall being perforated or to the instrument engaging in a co-lateral that has already been sectioned, or indeed by the instrument engaging in a vein other than the vein that is to be extracted. The light guidance indicates the proper path since it is always illuminated along the entire length of the fiber which serves simultaneously as a stripper, thus making it possible to perform the desired vein removal without any risk of going the wrong way.

In addition, the path is determined three-dimensionally, thus making it possible from the outside to inject local anesthetic accurately and to the right depth, given that local anesthetic is being used to an ever increasing extent in such surgery, which is often performed on an outpatient basis. Also, the quantity of local anesthetic used can be reduced because injection takes place at points that are better targeted.

The instrument manufactured in this way is generally intended for single use: it must be used under conditions that guarantee that it is sterile, thus making it completely safe in use.

Other advantages of the invention could be mentioned, but those given above suffice to demonstrate the novelty and the advantage of the invention.

BRIEF DESCRIPTION OF THE DRAWINGS

The following description and figures show an embodiment of the invention, but they are not limiting in any way: other embodiments are possible within the ambit of the scope and the extent of this invention, in particular concerning the shape of the distal end head, the number of optical fibers used, and the disposition of the operating channel.

MORE DETAILED DESCRIPTION

Figure 1:
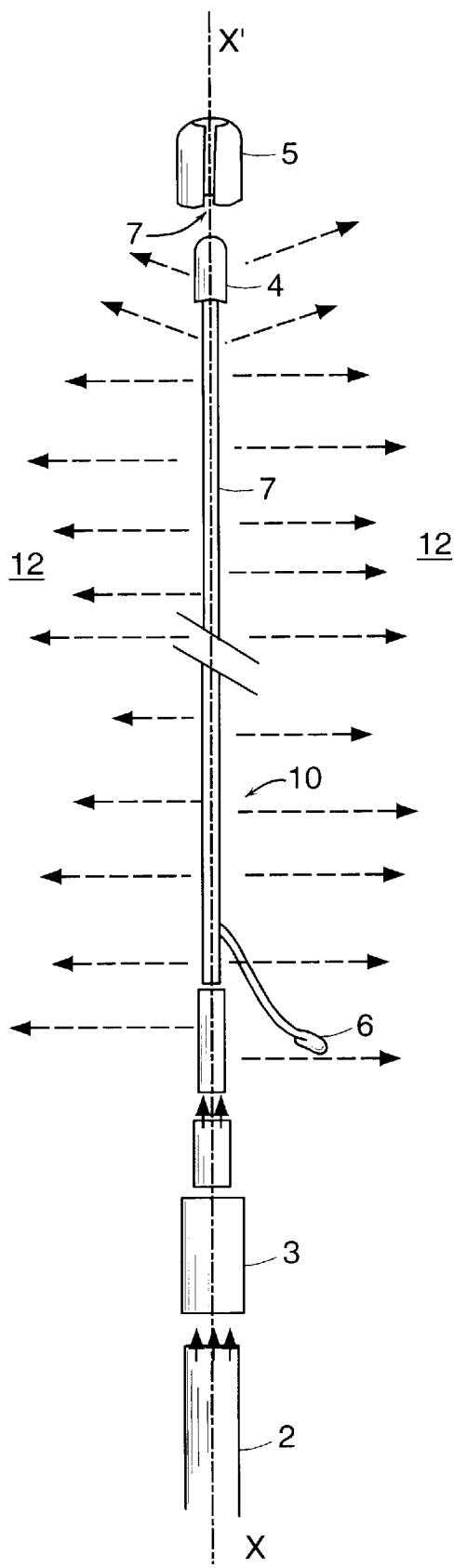
FIG. 1 is an overall view of an example of an instrument of the invention.

The instrument is mainly constituted by an elongate central body 10 constituted by at least one optical fiber or cable 1 that diffuses laterally 12, such as that described in above-mentioned patent No. FR 2 714 147, which is constituted by a core which, in presently known fibers, is essentially made of a polymer that is flexible, supple, and strong, such as polymethylmethacrylate, but which could be made of some other biocompatible material, such as polycarbonate.

The optical fiber or cable is connected at one of its ends to a light source 2 via a sheathed endpiece fitting 3.

Light generators and such light sources 2 are present in all operating theatres in any hospital: use can be made equally well of a halogen light generator or of a metal iodide generator and the color may be white, blue, or green.

The optical fiber system 12 that diffuses laterally possesses intrinsic physical qualities: cold light, complete absence of electricity, capable of operating without risk in a wet medium or when immersed. This eliminates thermal effects and risks of explosion, electrocution, or damage to surrounding structures.

The length of the instrument, of its central body, or of the optical fiber can lie in the range 0.80 meters (m) to 1.20 m, and the diameter of the central body or of the said optical fiber when there is only one of them is 1.5 mm to 2.5 mm depending on the bore of the vein that is to be illuminated and extracted.

Figure 2:
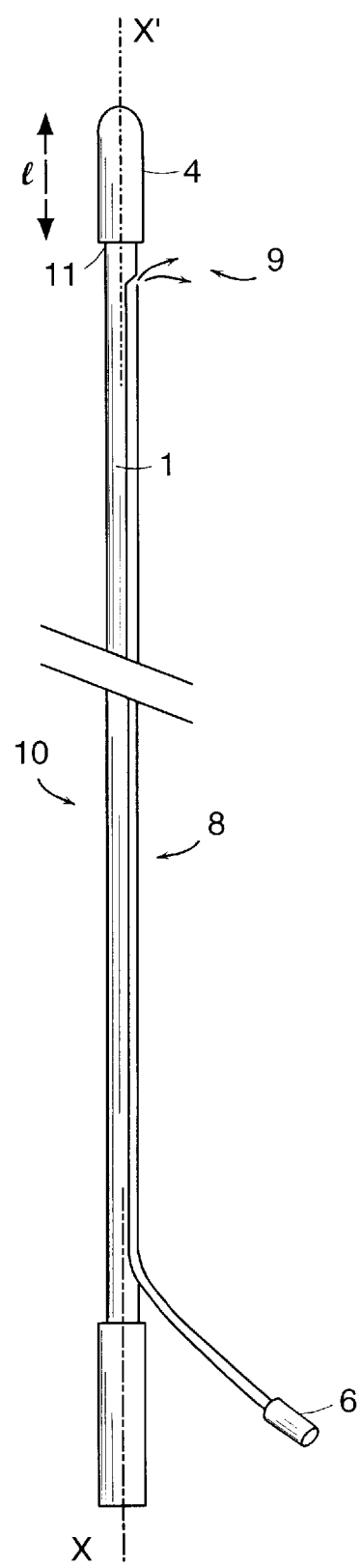
FIG. 2 is a more detailed view of the central body portion of the FIG. 1 instrument.

In a particular embodiment, the instrument is also provided with an operating channel 8 such as that shown in section in FIG. 2, making it possible, once the instrument is in place in a vein, optionally to inject liquids from the same end outside the body as the light source 2, merely by using a plastic syringe, e.g. a piston syringe which is inserted via an endpiece 6. The liquid injected may be a dye, a radiological substance, or a sclerosis-inducing substance which escapes 9 from the other or "distal" end of the instrument close to the transparent head 4 placed at the end of the central body 10.

The head 4 of the instrument may be cylindrical in shape having a length in the range 8 mm to 15 mm and a diameter in the range 3 mm to 3.5 mm, being rounded to a bullet shape at its end and making it possible to secure a thread behind the shoulder 11 thus created by the difference in diameter, which thread can be used for extracting the vein by invagination.

The thread must be long so that in the event of the vein breaking, the vein can be removed in the opposite direction.

To perform conventional stripping, a bullet-shaped cap 5 can be split on its side 7 and can be made of plastic having a diameter of 7 mm to 15 mm, being fittable on the head 4 by any snap-fastening system associated with said split 7 or equally fittable at the other end of the fiber 1, thus making exo-removal of veins possible in one direction or the other.

Said central body 10 may also be constituted:

either by a single one-piece fiber 1;

or by a single fiber and an operating channel placed to one side of the fiber 1, as in the embodiment shown in accompanying FIGS. 1 and 2, which operating channel can also be optionally pierced in said optical fiber;

or else by a plurality of touching parallel fibers that are twisted and/or stuck together and that are held together by any biocompatible transparent material, for example adhesive based on acrylic varnish, or by ultrasonic bonding, and said operating channel 8 can be assembled in said bundle made up of said fibers.

In any event, said central body 10 as a whole must constitute a single piece; when it is constituted by a single optical fiber 1 with said operating channel placed laterally relative thereto, the channel 8 may form a projection that then increases the overall diameter slightly, or it may be placed in a longitudinal groove formed along said optical fiber 1.

The instrument can also facilitate other vein removal techniques by providing localization in three dimensions: hook phlebectomies, vein removal on a rod, on a wick, vein removal with sclerosis.

It can help in locating where local anesthetic should be injected, both relative to the surface and in depth, thereby enabling the anesthetic to be administered exactly on site.

What is claimed is:

1. An instrument intended for locating and simultaneously removing a vein, comprising:

an elongated central body that comprises at least one optical fiber optically connectable at one end to a light source and provided at its distal end, that is not optically connectable to the light source, with a transparent head having a shoulder connecting it to the central body, said distal end including said transparent head being insertable into a vein, and said elongated central body being constructed to diffuse at least partially light laterally and radially relative to its longitudinal axis XX'; and said transparent head constructed and arranged to facilitate a partial removal of the vein.

2. An instrument according to claim 1, comprising a single one-piece optical fiber made of a polymer.

3. An instrument according to claim 1, including a plurality of touching optical fibers held together by any transparent material that is biocompatible.

4. An instrument according to claim 1, wherein said transparent head is a transparent cylinder rounded to a bullet shape.

5. An instrument according to claim 1, wherein said optical fiber is made of polymethylmethacrylate.

6. An instrument according to claim 1, including a hollow operating channel disposed along said central body for injecting liquids close to the transparent head at the distal end of said central body.

7. An instrument according to claim 1, including a bullet-shaped cap of a diameter not less than 7 mm, covering the transparent head at the distal end of said central body.

8. An instrument according to claim 7, wherein said bullet-shaped cap is split on its side and arranged for exo-removal of the vein.

9. An instrument according to claim 7, wherein said bulled-shaped cap is split on its side and arranged to be equally fittable at either end of said fiber to enable exo-removal of the vein in either direction.

10. An instrument according to claim 1, wherein the diameter of its central body lies in the range 1.5 mm to 2.5 mm and the transparent head is of outside diameter greater than that of the central body, creating said shoulder.

11. An instrument according to claim 1, wherein the central body behind the transparent head is helical or twisted in shape.

12. An instrument according to claim 1, wherein said optical fiber diffuses, over substantially its entire length, light laterally and radially relative to its longitudinal axis XX'.

13. An instrument according to claim 1, wherein said head is arranged to secure a thread behind said shoulder for extracting the vein by invagination.

14. An instrument according to claim 13, wherein said thread has a length that enables vein removal in an opposite direction when vein breaking occurs during said extraction.

15. An instrument according to claim 1, arranged for hook phlebectomy.

16. An instrument according to claim 1, arranged for vein removal on a rod.

17. An instrument according to claim 1, arranged for vein removal on a wick.

18. An instrument according to claim 1, arranged for vein removal with sclerosis.

19. A method for locating and simultaneously removing a vein, comprising:

providing an instrument including an elongated central body including an optical fiber with its proximal end optically connectable to a light source and its distal end connected to a transparent head having a shoulder;

introducing said elongated central body into a vein;

optically coupling light into said optical fiber to diffuse at least partially light laterally and radially relative to a longitudinal axis of said central body;

placing said transparent head within the vein near a valvulae of the vein; and removing a portion of the vein.

20. A method of claim 19 further including:

introducing contrast fluid through a hollow operating channel created along said elongated central body to a vein area near said distal end.

21. A method according to claim 19 further including:

introducing a sclerosis-inducing liquid through a hollow operating channel created along said elongated central body to a vein area near said distal end.

22. A method according to claim 19 wherein said removing of said portion of the vein includes performing hook phlebectomy.

23. A method according to claim 19 wherein said removing of said portion of the vein includes extracting the vein by invagination.

* * * * *